United States Patent [19]

Umezawa et al.

[11] 4,024,253

[45] May 17, 1977

[54] TREATMENT OF ELEVATED HISTAMINE AND URIC ACID LEVELS

[75] Inventors: Hamao Umezawa; Tomio Takeuchi, both of Tokyo; Akira Takamatsu; Kenji Kayahara, both of Yokohama, all of Japan

[73] Assignee: Zaidan Hojin Biseibutsu Kagaku Kenkyu Kai, Tokyo, Japan

[22] Filed: Apr. 5, 1976

[21] Appl. No.: 674,009

Related U.S. Application Data

[62] Division of Ser. No. 461,772, April 17, 1974, Pat. No. 3,973,038.

[30] Foreign Application Priority Data

Apr. 20, 1973 Japan .............................. 48-44922
Dec. 10, 1973 Japan ............................ 48-140111

[52] U.S. Cl. ................. 424/230; 424/308; 424/311

[51] Int. Cl.$^2$ ............... A61K 31/60; A61K 31/235; A61K 31/22

[58] Field of Search ................. 424/308, 311, 230

[56] References Cited

OTHER PUBLICATIONS

Chem. Abst. 8th Collective Index, vol. 66–75 (1967–1971) pp. 14983s and 32531s.

Primary Examiner—Sam Rosen
Attorney, Agent, or Firm—Herbert W. Taylor, Jr.

[57] ABSTRACT

Compounds having the general formula

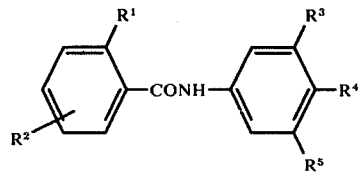

(the meanings of $R^1$, $R^2$, $R^3$, $R^4$ and $R^5$ are indicated hereinafter) and the pharmaceutically acceptable salts and esters thereof exhibit strong activities in inhibiting histidine decarboxylase and xanthine oxidase and are useful for treating elevated histamine and uric acid levels. One example is the compound of the formula

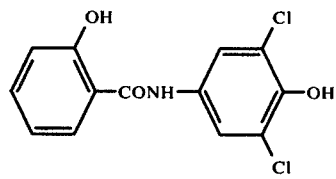

18 Claims, No Drawings

TREATMENT OF ELEVATED HISTAMINE AND URIC ACID LEVELS

CROSS-REFERENCE TO RELATED APPLICATION

This application is a division of our prior, copending application Ser. No. 461,772 filed Apr. 17, 1974 and issued Aug. 3, 1976 as U.S. Pat. No. 3,973,038.

BACKGROUND OF THE INVENTION

Several attempts have been made in the prior art to prepare specific metabolic inhibitors having specific chemotherapeutic applications. The use of 4-bromo-3-hydroxy-hippuric acid and cationic salts thereof has been described by Ellenbogen et al. in U.S. Pat. No. 3,646,121 as useful for inhibiting the formation of histamine in mammals by inhibiting histidine decarboxylase. Likewise, brocresin (4-bromo-3-hydroxybenzyloxamine phosphate) is a known inhibitor of histidine decarboxylase.

Allopurinol or 4-hydroxypyrazole-(3,4-d)-pyrimidine has been described in U.S. Pat. No. 3,474,098 as a useful therapeutic agent for inhibiting the production of uric acid in the purine catabolic cycle by interfering with the activity of xanthine oxidase, but several undesirable side effects have been reported and according to the Physician's Desk Reference 1973, pp. 651–652, the drug is suitable for only limited applications.

The present inventors discovered and disclosed in Japanese Pat. No. 96778/71 that lecanoric acid, abundantly produced by the fungus of genus Pyricularia, possesses a strong inhibitory activity to an enzyme, histidine decarboxylase, which catalyses the conversion of histidine to histamine. Lecanoric acid, in the previous specification is named as 4-O-(2,4-dihydroxy-6-methyl-benzoyl)-2-hydroxy-6-methyl-benzoic acid, but in this specification, we shall name it as 4'-carboxy-2,3'-dimethyl-4,6,5'-trihydroxyphenylbenzoate, however, was found by the inventors to be hydrolysed in animals thus exhibiting only weak anti-inflammatory activity. The inventors chemically synthesized the compounds of the present invention to seek compounds more stable in animals and having the said activities.

One of the compounds to meet the above requirements is N-(2,4-dihydroxybenzoyl)-4-aminosalicylic acid (which can also be named 4-carboxy-1', 3', 3-trihydroxybenzanilide) and its salts, on which a patent application was filed by these inventors as U.S. patent application Ser. No. 349,759 filed Apr. 10, 1973.

OBJECTS OF THE INVENTION

Accordingly, it is an object of this invention to provide a new compound having in vivo enzyme inhibition properties.

Another object of this invention is to provide a new compound useful for inhibiting the enzyme activity of histidine decarboxylase.

Still another object of this invention is to provide a new compound useful for inhibiting the enzyme activity of xanthine oxidase.

An additional object of this invention is to provide new pharmaceutical compositions and methods for the use thereof.

SUMMARY OF THE INVENTION

Briefly, the above and other objects are attained in one aspect of this invention by providing a compound having the formula

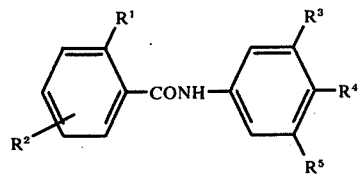

wherein
$R^1$ is

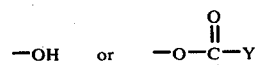

in which Y is lower alkyl or phenyl;

$R^2$ is substituted either at the 4'-position or at the 5'-position and is hydrogen, fluoro, bromo, chloro, hydroxy, lower alkyl or

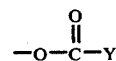

in which Y is lower alkyl or phenyl;

$R^3$ is chloro, bromo or lower alkyl;

$R^4$ is hydroxy, amine, lower alkoxy or

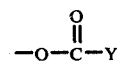

in which Y is lower alkyl or phenyl;

$R^5$ is hydrogen, fluoro, bromo, chloro, carboxyl, lower alkyl or

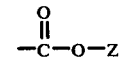

in which Z is lower alkyl; and the nontoxic, pharmaceutically acceptable metal salts of said compound in which $R^5$ is carboxyl.

Other embodiments of the present invention provide a. a pharmaceutical composition for administration to humans and animals comprising an amount of such a compound in an amount sufficient to inhibit the enzyme activity of histidine decarboxylase in vivo in combination with a pharmaceutically acceptable nontoxic carrier;

b. a method for chemotherapeutically treating a living animal having a biochemical disorder characterized by an abnormally high body level of histamine which comprises administering such a compound to said animal in a dosage sufficient to lower said histamine level; and c. a method for chemotherapeutically treating a living animal having a biochemical disorder characterized by an abnormally high body level of uric acid which comprises administering such a compound to said animal in a dosage sufficient to lower said uric acid level.

Other embodiments of the present invention are a. a compound having the formula

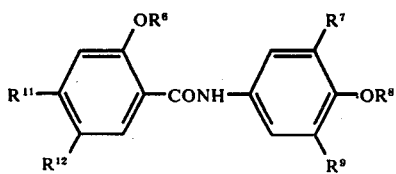

wherein
$R^6$ and $R^8$ are alike and are hydrogen, benzoyl or lower alkanoyl;
$R^7$ is chloro, bromo, methyl or ethyl;
$R^9$ is hydrogen, chloro, bromo, lower alkyl or lower alkoxy; and
one of $R^{11}$ and $R^{12}$ is hydrogen and the other is fluoro, bromo, chloro, hydroxy, lower alkanoyloxy, benzoyloxy, methyl or ethyl;

b. a compound having the formula

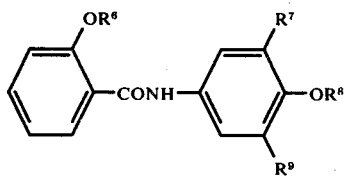

wherein
$R^6$ and $R^8$ are alike and are hydrogen, benzoyl or lower alkanoyl;
$R^7$ is chloro, bromo, methyl or ethyl and
$R^9$ is hydrogen, chloro, bromo, lower alkyl or lower alkoxy;

c. a compound having the formula

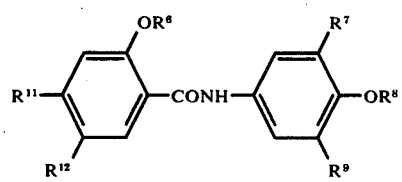

wherein
$R^6$ is hydrogen, benzoyl or lower alkanoyl,
$R^8$ is methyl or ethyl,
$R^7$ is chloro, bromo, methyl or ethyl;
$R^9$ is hydrogen, chloro, bromo, lower alkyl or lower alkoxy; and
one of $R^{11}$ and $R^{12}$ is hydrogen and the other is fluoro, bromo, chloro, hydroxy, lower alkanoyloxy, benzoyloxy, methyl or ethyl; and d. a compound having the formula

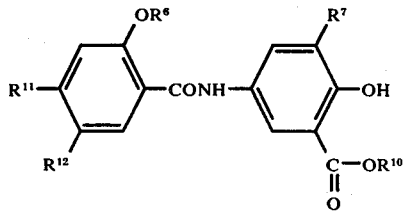

wherein
$R^6$ is hydrogen, benzoyl or lower alkanoyl;
$R^7$ is chloro, bromo, methyl or ethyl;
$R^{10}$ is hydrogen, lower alkyl, sodium, potassium, calcium magnesium or aluminum; and
one of $R^{11}$ and $R^{12}$ is hydrogen and the other is fluoro, bromo, chloro, hydroxy, lower alkanoyloxy, benzoyloxy, methyl or ethyl; and, for each such group of compounds, a. a pharmaceutical composition for administration to humans and animals comprising an amount of such a compound in an amount sufficient to inhibit the enzyme activity of histidine decarboxylase in vivo in combination with a pharmaceutically acceptable nontoxic carrier;

b. a method for chemotherapeutically treating a living animal having a biochemical disorder characterized by an abnormally high body level of histamine which comprises administering such a compound to said animal in a dosage sufficient to lower said histamine level; and c. a method for chemotherapeutically treating a living animal having a biochemical disorder characterized by an abnormally high body level of uric acid which comprises administering such a compound to said animal in a dosage sufficient to lower uric acid level.

Preferred embodiments of the present invention are the two compounds having the formulae

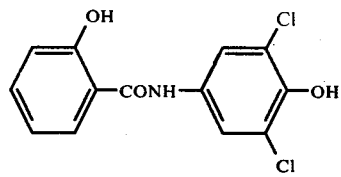

and

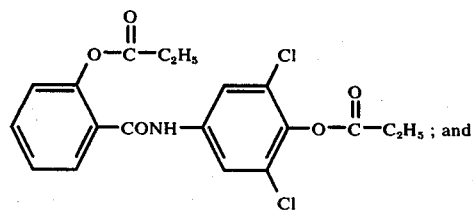

a. a pharmaceutical composition for administration to humans and animals comprising an amount of each such compound in an amount sufficient to inhibit the enzyme activity of histidine decarboxylase in vivo in combination with a pharmaceutically acceptable non-toxic carrier;

b. a method for chemotherapeutically treating a living animal having a biochemical disorder characterized by an abnormally high body level of histamine which comprises administering each such compound to said animal in a dosage sufficient to lower said histamine level; and c. a method for chemotherapeutically treating a living animal having a biochemical disorder characterized by an abnormally high body level of uric acid which comprises administering each such compound to said animal in a dosage sufficient to lower said uric acid level.

The present compounds are obtained as crystals of white to light brown needles, prism or scale which melt at about 135° to 250° C. with some exceptions. Physical properties of some compounds according to the invention are given as follows:

1. 3,5-Dichloro-2', 4-dihydroxybenzanilide is produced by deacetylation of the compound synthesized by condensation between 4-amino-2,6-dichlorophenol and acetylsalicyloyl chloride which is prepared by reacting acetylsalicylic acid with thionyl chloride.

The compound melts at the temperature between 217°–218° C. On silica-gel thin-layer chromatography (DC - Fertigplatten Kieselgel 60F-254: Merck Company, Germany) developed with a solvent system of benzene: methanol:acetic acid (10:1:0:1), a single spot was obtained at 0.34 of Rf value. Elementary analysis (as $C_{13}H_9O_3NCl_2$); Calcd. for C, 52.0; H, 3.2; O, 16.5; N, 4.6; Cl, 23.7. Found: C, 52.3; H, 3.0; O, 16.3; N, 4.7; Cl, 23.8.

2. 3-carboxy-5-chloro-2', 4-dihydroxybenzanilide is synthesized by deacetylation of the compound prepared by condensation between 3-chloro-5-aminosalicylic acid and acetylsalicyloyl chloride which is produced from the reaction of acetylsalicylic acid with thionyl chloride.

The compound melts at 257°–260° C. On silica-gel thin-layer chromatography by the solvent system of benzene:methanol:acetone (1:1:1), a single spot was obtained at the Rf value 0.64. Elementary analysis (as $C_{14}H_{10}O_5NCl$); Calcd.: C, 54.1; H, 3.5; O, 26.5; N, 4.5; Cl, 11.4. Found: C, 54.6; H, 3.3; O, 26.0; N, 4.6; Cl, 11.5.

3. 3,5-Dichloro-2', 4-dipropionyloxybenzanilide is obtained by esterification of 3,5-dichloro-2', 4-dihydroxybenzanilide with propionic acid. The former compound is synthesized by deacetylation of the product resulting from the condensation between acetylsalicyloyl chloride and 4-amino-2,6-dichlorophenol. The compound melts at 108°–110° C. The thin-layer chromatography on silica-gel using a developing solvent system of benzene:methanol:acetic acid (10:1:0.1) gave the Rf value 0.69. Elementary analysis for $C_{19}H_{17}O_5NCl_2$ gave the value; Calcd.: C, 55.5; H, 4.4; O, 19.6; N, 3.5; Cl, 17.0. Found: C, 55.6; H, 4.2; O, 19.5; N, 3.4; Cl, 17.3.

4. 3,5-Dichloro-2', 4-dihydroxy-5'-fluorobenzanilide was obtained by condensation between 2-hydroxy-5-fluorobenzoyl chloride and 3,5-dichloro-4-hydroxyaniline.

The melting point of the compound is 227°–229° C. On silica-gel thin-layer chromatography it gives a single spot at Rf value 0.90 with developing solvent of benzene:ethyl acetate:formic acid (5:4;1). Elementary analysis (as $C_{13}H_8O_3N.Cl_2F$) Calcd.: C, 49.4; H, 2.5; O, 15.2; N, 4.4; Cl, 22.5; F, 6.0. Found: C, 49.3; H, 2.8; O, 15.4; N, 4.7; Cl, 22.1; F, 5.7.

The physical properties of some other compounds in accordance with this invention will be given in the embodiments described hereinunder.

PREPARATION

The compounds of the invention, as expressed in the general formula above are prepared by condensation of two ring moieties, i.e., between the salicylic acid derivative having $R_1$ and $R_2$ groups or atoms on the benzene ring and the aniline derivative having $R_3$, $R_4$ and $R_5$ groups or atoms. Those R groups if desired can be modified to salts or esters before or after the said condensation. For example, when R is hydroxyl, it is converted to its esters by esterification with the desired carboxyl group or acid-halogenide group, and when R is carboxyl, it is made to its esters or to its salts using a number of conventional methods and conditions.

In view of the methods employed in this invention, most of principally known methods for amide condensation, esterification or salt formation are employable.

In the condensation reaction between the salicylic acid derivative and the aniline derivative, a variety of reactions for peptide formation, e.g. esterification using acid halogenides, or anhydrous acids, or active esterification are applicable. However, from industrial and economical view points, the esterification using acid halogenides or anhydrous acids are preferred for the specific compounds presented herein, on which are given the detailed description:

1. Dehydrohalogenation Condensation

In this method, the carbonyl group of the salicylic acid derivatives is made to its acid halogenide, to which the amine group of the aniline derivatives is condensed, i.e. dehydrohalogenation, through the following steps:

1. Masking or Protecting of the hydroxyl group in the salicylic acid compounds

The hydroxyl group(s) on salicyclic acid or its derivatives may be masked or protected for prevention of undesired side reactions by such groups as acyl e.g. acetyl; carboalkoxy, e.g. carbomethoxy, carboethoxy; carbobenzoxy; trityl; trimethyl silyl; tetrahydropyranyl or other conventional protective groups which is, if desired, easily removable from the condensation product.

2. Acid-halogenation of the carboxyl group in the masked salicyclic acid derivatives.

The carboxyl group in the compounds from step (1) is made to its acid halogenide by conventionally employed techniques using halogenating agents such as thionyl chloride, phosphorus halogenide, sulfuryl chloride.

3. Condensation

The acid halide compounds from step (2) and the aimed aniline compounds are condensed by way of dehydrohalogenation type condensation to form the amide compounds. Various conventionally known techniques and conditions for amide formation are employable.

4. De-masking

When desired, the masking or protective group introduced by step (1) may be removed from the amide compound formed in step (3) conventionally employed technique.

2. Direct Condensation

The salicylic acid compounds masked or unmasked, without converting to the acid halogenated form as shown in 1 - (2), may be directly condensed to the aniline derivative with aid of dehydrating condensation agents such as dicyclohexyl carbodiimide or thionyl chloride.

Conventional techniques and conditions for this type of condensation are employable (J. C. Sheehan, D. D. H. Young; J. Am. Chem. Soc. 80, 1158 (1958).

3. Esterification

The compounds obtained by condensation, whose hydroxyl group(s) is masked or demasked, can be led to its ester by conventionally employed technique of esterification: Various compounds possessing free carboxyl group or acid halogenated group are employable for esterification of the condensed product with aid of proper dehydrating or dehydrohalogenating agents.

Vice-versa, esterification of free carboxyl group(s) on the condensation product may be achieved in similar manner by use of the compounds with free hydroxy group e.g. alcohols.

4. Salt formation

The condensation products having free carboxyl group(s) may be converted to their simple or complex salt addition forms. Preferably employed alkalis for salt formation include alkali and alkaline earth metals e.g. sodium, potassium, magnesium, calcium and other pharmaceutically acceptable metals such as aluminium. Various techniques are employable for these salt formation that are conventional for the simple or complex salt formation of aromatic carboxylic acids.

The desired products forming and existing in the reaction mixture may be isolated and purified by conventional methods of isolation for free aromatic acids, their amides, their esters and their salts with some modifications suitable for the specific products.

The compounds prepared in this invention are identified by physical characterization e.g. melting point, elementary analysis, infrared spectra, nuclear magnetic resonance spectra and so on.

Biological Properties

1. Inhibition of Histidine Decarboxylase:

The compounds of this invention are strong inhibitors of histidine decarboxylase. The inhibition rate was determined in a test-tube incubation system consisting of $2.5 \times 10^{-4}$ M.L-histidine-2-$^{14}$C($1.0 \times 10^5$ cpm), $3.7 \times 10^{-5}$ M pyridoxal phosphate, 0.1 ml. of histidine decarboxylase (a crude enzyme preparation obtained from fetal rats, 4 mg. protein/ml.), and 0.1 ml. of 0.67 M phosphate buffer pH 6.8, to which the test compound in aqueous solution was added and the total volume was brought to 1 ml. with buffer. After two hours of incubation at 37° C., the histamine 2-$^{14}$C formed was collected on an ion exchange resin ("Amberlite" CG-50, ammonia type) from which, after washing with water, the histamine was liberated in 1N aqueous ammonia solution and radioactivity was measured.

The $ID_{50}$ values, the amount of inhibitor giving 50% inhibition of the enzyme activity in this assay system, are given in Table 1-a for the representative compounds according to this invention.

Table 1

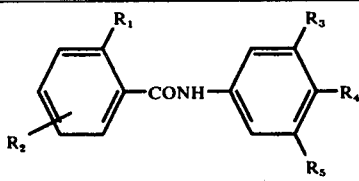

| Compound Number | $R_1$ | $R_2$ | $R_3$ | $R_4$ | $R_5$ | a Histidine Decarboxylase Inhibition $ID_{50}$ (mol/l) | b Xanthine Oxidase Inhibition $ID_{50}$ (mol/l) |
|---|---|---|---|---|---|---|---|
| 1 | OH | H | Cl | OH | Cl | $2.2 \times 10^{-8}$ | $1.3 \times 10^{-4}$ |
| 2 | OH | H | Cl | OH | H | $2.5 \times 10^{-6}$ | $1.0 \times 10^{-4}$ |
| 3 | OH | H | Br | OH | Br | $2.3 \times 10^{-8}$ | $8.1 \times 10^{-5}$ |
| 4 | OH | 4-OH | Cl | OH | Cl | $2.8 \times 10^{-8}$ | $7.4 \times 10^{-5}$ |
| 5 | OH | 4-OH | Br | OH | H | $3.0 \times 10^{-8}$ | $6.8 \times 10^{-5}$ |
| 6 | OH | H | Br | OH | COOH | $2.6 \times 10^{-7}$ | $4.2 \times 10^{-4}$ |
| 7 | OH | H | Cl | OH | COOH | $1.1 \times 10^{-7}$ | $2.4 \times 10^{-4}$ |
| 8 | OH | 4-$CH_3$ | Cl | OH | Cl | $9.6 \times 10^{-8}$ | $9.2 \times 10^{-5}$ |
| 9 | OH | 4-F | Cl | OH | Cl | $8.9 \times 10^{-8}$ | $9.6 \times 10^{-5}$ |
| 10 | OH | 5-F | Cl | OH | Cl | $2.3 \times 10^{-7}$ | $2.8 \times 10^{-4}$ |
| 11 | OH | H | Cl | $OCH_3$ | Cl | $2.1 \times 10^{-7}$ | $9.0 \times 10^{-5}$ |

| Compound Number | c Edema-Suppression: $ED_{30}$ (mg./kg.) | | d Analgesic Activity: Stretching Count (20 minutes) | | e Antipyretic Activity: Elevation of Body Temperature (° C.) | |
|---|---|---|---|---|---|---|
| | Oral | I.p. | 50 mg./kg. | 200 mg./kg. | 2 hrs. | 4 hrs. |
| 1 | 17.5 | 4.5 | 11 | 4 | 0.6 | 0.5 |
| 2 | 25 | 10.5 | 30 | 12 | 0.6 | 0.5 |
| 3 | 20 | 5.1 | 17 | 6 | 0.6 | 0.5 |
| 4 | 20.5 | 4.6 | 13 | 6 | 0.5 | 0.4 |
| 5 | 24 | 5.9 | 14 | 6 | 0.5 | 0.4 |
| 6 | 25 | 7.5 | 25 | 12 | 0.5 | 0.5 |
| 7 | 26 | 7.7 | 40 | 14 | 0.6 | 0.5 |
| 8 | 27 | 7.5 | 40 | 21 | 0.6 | 0.5 |
| 9 | 24 | 7.7 | 35 | 20 | 0.6 | 0.6 |

Table 1-continued

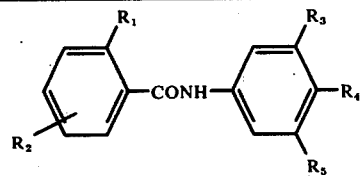

| | | | | | | |
|---|---|---|---|---|---|---|
| 10 | 29 | 7.0 | 35 | 20 | 0.6 | 0.5 |
| 11 | | 6.5 | | | | |

| Compound Number | $R_1$ | $R_2$ | $R_3$ | $R_4$ | $R_5$ | a<br>Histidine Decarboxylase Inhibition $ID_{50}$ (mol/l) | b<br>Xanthine Oxidase Inhibition $ID_{50}$ (mol/l) |
|---|---|---|---|---|---|---|---|
| 12 | OH | H | Cl | OH | $CH_3$ | $1.2 \times 10^{-7}$ | $1.1 \times 10^{-4}$ |
| 13 | OH | H | Cl | OH | F | $2.3 \times 10^{-7}$ | $2.1 \times 10^{-4}$ |
| 14 | OH | H | $CH_3$ | OH | $CH_3$ | $1.1 \times 10^{-6}$ | $4.3 \times 10^{-4}$ |
| 15 | OH | 4-OH | Br | $OC_2H_5$ | Cl | $3.1 \times 10^{-7}$ | $3.1 \times 10^{-4}$ |
| 16 | OH | 4-OH | $C_2H_5$ | $OCH_3$ | F | $8.1 \times 10^{-7}$ | $4.6 \times 10^{-4}$ |
| 17 | OH | 4-$C_2H_5$ | Br | OH | $C_2H_5$ | $4.6 \times 10^{-7}$ | $4.1 \times 10^{-4}$ |
| 18 | OH | 5-$C_2H_5$ | Br | OH | $C_2H_5$ | $7.1 \times 10^{-7}$ | $3.5 \times 10^{-4}$ |
| 19 | OH | 4-Br | $CH_3$ | OH | COOH | $3.3 \times 10^{-7}$ | $4.1 \times 10^{-4}$ |
| 20 | OH | 5-Br | Cl | OH | H | $5.8 \times 10^{-7}$ | $3.9 \times 10^{-4}$ |
| 21 | OH | 4-F | Cl | $OC_2H_5$ | H | $5.0 \times 10^{-7}$ | $3.9 \times 10^{-4}$ |
| 22 | OH | 4-$CH_3$ | Br | OH | Br | $8.0 \times 10^{-7}$ | $5.6 \times 10^{-4}$ |

| Compound Number | c<br>Edema-Suppression: $ED_{30}$ (mg./kg.) | | d<br>Analgesic Activity: Stretching Count Elevation of Body (20 minutes) | | e<br>Antipyretic Activity: Temperature (°C.) | |
|---|---|---|---|---|---|---|
| | Oral | I.p. | 50 mg./kg. | 200 mg./kg. | 2 hrs. | 4 hrs. |
| 12 | | 6.3 | | | | |
| 13 | | 6.5 | | | | |
| 14 | | 9.0 | | | | |
| 15 | | 7.7 | | | | |
| 16 | | 9.2 | | | | |
| 17 | | 8.7 | | | | |
| 18 | | 7.5 | | | | |
| 19 | | 8.0 | | | | |
| 20 | | 8.7 | | | | |
| 21 | | 8.2 | | | | |
| 22 | | 9.5 | | | | |

| Compound Number | $R_1$ | $R_2$ | $R_3$ | $R_4$ | $R_5$ | a<br>Histidine Decarboxylase Inhibition $ID_{50}$ (mol/l) | b<br>Xanthine Oxidase Inhibition $ID_{50}$ (mol/l) |
|---|---|---|---|---|---|---|---|
| 23 | OH | 5-OH | Cl | OH | COOH | $5.0 \times 10^{-7}$ | $4.3 \times 10^{-4}$ |
| 24 | OH | H | Cl | $NH_2$ | Cl | $1.4 \times 10^{-7}$ | $1.3 \times 10^{-4}$ |
| 25 | OH | 4-Cl | Cl | $OCH_3$ | F | $5.0 \times 10^{-7}$ | $4.4 \times 10^{-4}$ |
| 26 | OH | 5-Cl | Cl | $OCH_3$ | F | $6.9 \times 10^{-7}$ | $2.2 \times 10^{-4}$ |
| 27 | OH | H | Br | OH | $COOC_3H_7$ | $1.4 \times 10^{-7}$ | $1.5 \times 10^{-4}$ |
| 28 | OH | 4-$CH_3$ | $C_2H_5$ | OH | $COOCH_3$ | $7.9 \times 10^{-7}$ | $4.7 \times 10^{-4}$ |
| 29 | OH | 5-$CH_3$ | $C_2H_5$ | OH | $COOCH_3$ | $9.8 \times 10^{-7}$ | $5.1 \times 10^{-4}$ |
| 30 | $OCOCH_3$ | H | Cl | $OCOCH_3$ | Cl | $2.4 \times 10^{-8}$ | $2.7 \times 10^{-4}$ |
| 31 | $OCOCH_2-CH(CH_3)_2$ | H | Cl | $OCOCH_2-CH(CH_3)_2$ | Cl | $1.7 \times 10^{-8}$ | $1.3 \times 10^{-4}$ |
| 32 | OCO-Ph | H | Cl | OCO-Ph | Cl | $4.5 \times 10^{-8}$ | $9.9 \times 10^{-5}$ |

Table 1-continued

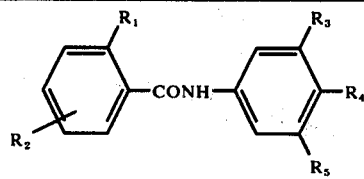

| Compound Number | Edema-Suppression: ED$_{30}$ (mg./kg.) | | Analgesic Activity: Stretching Count (20 minutes) | | Antipyretic Activity: Elevation of Body Temperature (° C.) | |
|---|---|---|---|---|---|---|
| | Oral | I.p. | 50 mg/kg. | 200 mg./kg. | 2 hrs. | 4 hrs. |
| | c | | d | | e | |
| 23 | | 9.4 | | | | |
| 24 | | 6.5 | | | | |
| 25 | | 7.7 | | | | |
| 26 | | 7.5 | | | | |
| 27 | | 5.0 | | | | |
| 28 | | 8.8 | | | | |
| 29 | | 10 | | | | |
| 30 | 19 | 4.5 | 14 | 4 | 0.5 | 0.5 |
| 31 | 15 | 4.0 | 13 | 4 | 0.6 | 0.5 |
| 32 | 17 | 4.6 | 14 | 7 | 0.6 | 0.5 |

| Compound Number | R$_1$ | R$_2$ | R$_3$ | R$_4$ | R$_5$ | a Histidine Decarboxylase Inhibition ID$_{50}$ (mol/l) | b Xanthine Oxidase Inhibition ID$_{50}$ (mol/l) |
|---|---|---|---|---|---|---|---|
| 33 | OCOC$_2$H$_5$ | H | Cl | OCOC$_2$H$_5$ | Cl | 3.9 × 10$^{-8}$ | 3.1 × 10$^{-4}$ |
| 34 | OCOCH$_3$ | 4-OH | Cl | OCOCH$_3$ | CH$_3$ | 3.9 × 10$^{-7}$ | 3.6 × 10$^{-4}$ |
| 35 | OCOCH$_3$ | 5-OH | Cl | OCOCH$_3$ | CH$_3$ | 6.0 × 10$^{-7}$ | 1.3 × 10$^{-4}$ |
| 36 | OCOC$_2$H$_5$ | 4-OH | Br | OCOC$_2$H$_5$ | H | 4.9 × 10$^{-7}$ | 3.9 × 10$^{-4}$ |
| 37 | OCOCH$_3$ | 4-F | CH$_3$ | OCOCH$_3$ | Br | 4.2 × 10$^{-7}$ | 2.1 × 10$^{-4}$ |
| 38 | OCOC$_2$H$_5$ | H | Cl | NH$_2$ | Cl | 2.0 × 10$^{-7}$ | 1.3 × 10$^{-4}$ |
| 39 | OCOCH$_3$ | 4-OCOCH$_3$ | Cl | OH | Cl | 1.9 × 10$^{-7}$ | 1.6 × 10$^{-4}$ |
| 40 | OCOCH$_3$ | 5-OCOCH$_3$ | Cl | OH | Cl | 3.1 × 10$^{-7}$ | 4.0 × 10$^{-4}$ |
| 41 | OCO—C$_6$H$_5$ | H | Cl | OH | COOC$_2$H$_5$ | 3.2 × 10$^{-7}$ | 3.3 × 10$^{-4}$ |

| Compound Number | Edema-Suppression: ED$_{30}$ (mg./kg.) | | Analgesic Activity: Stretching Count (20 minutes) | | Antipyretic Activity: Elevation of Body Temperature (° C.) | |
|---|---|---|---|---|---|---|
| | Oral | I.p. | 50 mg/kg. | 200 mg./kg. | 2 hrs. | 4 hrs. |
| | c | | d | | e | |
| 33 | 15 | 4.7 | 12 | 5 | 0.6 | 0.5 |
| 34 | | 7.5 | | | | |
| 35 | | 7.7 | | | | |
| 36 | | 8.3 | | | | |
| 37 | | 8.6 | | | | |
| 38 | | 5.9 | | | | |
| 39 | | 6.2 | | | | |
| 40 | | 6.3 | | | | |
| 41 | | 7.6 | | | | |

| Compound Number | R$_1$ | R$_2$ | R$_3$ | R$_4$ | R$_5$ | a Histidine Decarboxylase Inhibition ID$_{50}$ (mol/l) | b Xanthine Oxidase Inhibition ID$_{50}$ (mol/l) |
|---|---|---|---|---|---|---|---|
| 42 | OCOC$_3$H$_7$ | 4-OCOC$_3$H$_7$ | Cl | NH$_2$ | COOCH$_3$ | 5.1 × 10$^{-7}$ | 2.6 × 10$^{-4}$ |
| 43 | OCOC$_2$H$_5$ | 5-OCOC$_2$H$_5$ | Cl | NH$_2$ | COOCH$_3$ | 5.3 × 10$^{-7}$ | 3.1 × 10$^{-4}$ |

Table 1-continued $$\text{structure: } R_1, R_2 \text{ on first ring, -CONH- linker, } R_3, R_4, R_5 \text{ on second ring}$$

| Compound | $R_1$ | $R_2$ | $R_3$ | $R_4$ | $R_5$ | a | b |
|---|---|---|---|---|---|---|---|
| 44 | OCOCH₃ | H | Cl | OH | COOC₂H₅ | $2.3 \times 10^{-7}$ | $2.2 \times 10^{-4}$ |

| | c | | d | | e | |
|---|---|---|---|---|---|---|
| | Edema-Suppression: $ED_{30}$ (mg./kg.) | | Analgesic Activity: Stretching Count (20 minutes) | | Antipyretic Activity: Elevation of Body Temperature (° C.) | |
| Compound Number | Oral | I.p. | 50 mg./kg. | 200 mg./kg. | 2 hrs. | 4 hrs. |
| 42 | | 7.8 | | | | |
| 43 | | 7.9 | | | | |
| 44 | | 8.0 | | | | |
| Phenyl butazone | 22 | 8.0 | | | | |
| Aminopyrine | | | 8 | 2 | 0.4 | 0.3 |
| Control (no drug) | | | | 53 | 1.2 | 1.6 |

2. Inhibition of Xanthine Oxidase

The compounds of this invention also exhibit a strong inhibition of xanthine oxidase. The inhibition of xanthine oxidase was determined by a modification of H. M. Kalcher's method described in J. Biol. Chem. 169: 429 (1947). The incubation mixture contains $3.7 \times 10^{-5}$M hypoxanthine, $5 \times 10^{-3}$M phosphate buffer pH 7.4, 0.1 ml. xanthine oxidase solution (containing 1 mg. protein or 0.0005 Unit of the enzyme) and the test compound in a total volume of 3 ml. The enzyme solution was from either a rat liver enzyme prepared by centrifuge fractionation, or a commercially obtained milk enzyme. One Unit of the enzyme is defined as forming one micromole of uric acid per minute for xanthine at 25° C., pH 7.4. The incubation was made at 25° C. and the amount of uric acid thus formed was determined at one minute intervals for five minutes by measuring the specific absorption of uric acid at 290 m$\mu$. The inhibition rate (in percent) was obtained by the following calculation:

$$\text{Inhibition Rate} = \frac{C-S}{C} \times 100$$

S = Increase in the optical density at 290 m$\mu$ from 1 to 5 minutes in the presence of the test compound.
C = The optical density value in the absence of the test compound.

In the above system, the concentrations of the compounds required to inhibit 50% of the enzyme activity ($ID_{50}$) are given in Table 1-b.

3. Inhibition of Carrageenin-Induced Edema in Rats

Male rats of Wistar Strain having 165 gm. mean body weight were given the test compound in dosages of 3.1, 13.5 or 50 mg./kg. by oral or intraperitoneal (i.p.) route of administration. Each experimental group consisted of 5 animals. One hour after the drug dosing, 0.1 ml. of a 1% carrageenin solution in saline was subcutaneously injected into left foot pad and the swelling volume of the thusly induced edema was measured 3 and 5 hours after induction and compared to a control group which received no anti-inflammatory drug and to a group which received aspirin.

The $ED_{30}$ values, i.e. an effective dose of the drug to reduce edema volume by 50% relative to the negative control group, for some of the compounds are given in Table 1-c and show that compounds of this invention have strong anti-inflammatory activity.

4. Analgesic Activity in mice

Male mice of the DDY Strain having mean body weight of 20 g. were divided to the groups of 10 animals each, to which compounds of this invention or aminopyrine in saline solution were administered intraperitoneally (i.p.). The dosage was 200, 50 or 12.5 mg./kg. Then 30 minutes later, 0.2 ml. per 20 g. body weight of 0.7% acetic acid in saline was injected intraperitoneally and the number of characteristic stretching movements counted for 20 minute period and compared with a control group receiving no analgesic. The results are shown in Table 1-d.

5. Antipyretic Activity in Pyrexia-Induced Rabbits

Common white male Japanese rabbits, 2.0–3.0 kg. body weight, were injected through the ear vein with 20 $\mu$g./kg. of a pyrexia inducer TTG No. 2, purified polysaccharide preparation obtained from Pseudomonas aeruginosa (marketed by Fujisawa Pharmaceutical Company, Japan), and the body temperature was monitored with a rectal thermister-type thermometer. Three hours prior to the TTG injection four rabbits in each experimental section orally received the test drug in the dose of 200 mg./kg. One group received aspirin in a dose of 100 mg./kg and a control group no drug. The results show in Table 1-e in terms of elevation of body temperature measured at 2 and 4 hours after TTG injection.

6. Effect on the Anaphylactic Shock in Mice

DDY Strain mice were sensitized by subcutaneous injection of a mixture of 0.1 ml. (100 $\mu$g.) egg albumin (Nutritional Biochemical Corp. U.S.A., 5 times crystallized) and 0.1 ml. Freund's complete adjuvant (Difco Co., U.S.A.) in saline. The mice were used for the test 3 months thereafter. The sensitized animals were divided in 3 groups of 4 animals each, which were subcutaneously administered the test compound several times before antigen challenge to cause anaphylactic shock. Group 1 received 100 mg./kg. 19 hours before and 50 mg./kg. 9, 4 and 1 hour before challenge. Group 2 received 100 mg./kg. 9 hours before and 50 mg./kg. 4 and 1 hour before challenge. Group 3 was a control group and received only saline solution.

Following challenge by intravenous injection of 100 μg of egg albumin all animals in the control group died from shock within 15-25 minutes. In all cases in the groups receiving the test drugs, the emerging time of shock symptoms was much delayed and a half of the animals survived (Table 2).

Table 2

|  | Time: | Time in minutes after Challenge | | | |
| --- | --- | --- | --- | --- | --- |
|  |  | Mouse 1 | Mouse 2 | Mouse 3 | Mouse 4 |
| Group 1 | | | | | |
| compound 1 | Symptoms emerged | 15 | 20 | | |
| in Table 1 | Died | 30 | 35 | Survived | Survived |
| compound 33 | Symptoms emerged | 10 | 25 | 30 | |
| in Table 1 | Died | 30 | Survived | Survived | Survived |
| Group 2 | | | | | |
| compound 1 | Symptoms emerged | 35 | 10 | 25 | 20 |
| in Table 1 | Died | Survived | 30 | Survived | 40 |
| compound 33 | Symptoms emerged | 20 | 20 | 30 | 20 |
| in Table 1 | Died | 40 | 45 | Survived | 40 |
| Group 3 | | | | | |
|  | Symptoms emerged | 5 | 3 | 7 | 3 |
|  | Died | 15 | 20 | 25 | 20 |
|  |  | (minutes after induction) | | | |

7. Toxicity

The acute toxicity was determined for oral and intraperitoneal administration with mice and rats (6 mice and 2 rats in one dose group), and the $LD_{50}$ value, i.e., the single application dose killing 50% of the test animals, was estimated.

In mice, the values ranged 750-2900 mg./kg (e.g. Compound 1 in Table 1 was 2400 mg./kg.) for intraperitoneal and more than 3600 mg./kg. for oral administration. In rats, the values ranged 700-2350 mg./kg. for oral administration. In rats, the values ranged 700-2350 mg./kg. (e.g. Compound 1 was 2200 mg./kg.) and more than 4200 mg./kg. for respective administration. Compounds 3, 5, 6, 15, 19, 20, 22, 24, 42 and 43 in Table 1 appear comparatively more toxic than the others. The salt addition forms (e.g. sodium, calcium, aluminum for the compounds with the carboxylic group show less toxicity than the acid forms.

The compounds 1 and 33 in Table 1 were given orally or intraperitoneally to rats (average weight 150 g.) in daily doses of 3.1, 12.5, 50 and 200 mg./kg. respectively for 32 consecutive days, the weight gain was normal and no particular disease symptoms or abnormality attributable to the drug dosing was noted.

Accordingly, the compounds of this invention have a low acute to subacute toxicity profile.

Pharmaceutical Utility

Due to their enzyme inhibiting activity, the compounds of this invention are useful as histidine decarboxylase and/or xanthine oxidase inhibiting agents in human and veterinary medicine. These compounds are useful in the treatment of various diseases and disorders in which excess histamine or uric acid play possible roles. Such diseases and disorders include but are not limited to various types of inflammation and pain, pyrexia, allergic diseases such as asthma and nettle rash, dermatological diseases, mastocytoma, hyperacidity, rheumatism and arthritis and also hyperuricacidemias such as caused by gout and urate stone. In addition to their use in vitro, they can be employed, for example, in the topical, enteral, or parenteral therapy of inflammations in substantially the same manner as a known compound, e.g. phenylbutazone, mephenamic acid, bucolome.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily, e.g., peanut oil, olive oil and sesame oil, or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being one or more of lactose, corn starch, potato starch, gelatin, agar, pectin, talc, calcium carbonate or sodium carbonate. A syrup, elixir or the like can be used wherein a sweetened vehicle is employed. Sustained release compositions can be formulated including those wherein the active compound is protected with differentially degradable coatings, etc., as well as compositions wherein the carrier or diluent itself includes a time delay material, e.g., glyceryl monostearate or glyceryl distearate, either along or with wax.

Generally, the compounds of this invention are dispensed in unit dosage form comprising 1-2500 mg. of a pharmaceutical carrier per unit dosage, and the amount of active agent of the invention per unit dosage is about 50 to 1250 mg.

For topical application, these are employed as nonsprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are srapyable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incorporated in topical formulations in a concentration of about 0.1 to 5 weight percent.

The compounds of this invention are generally administered to animals, including but not lmited to mammals, e.g. humans, livestock, household pets, laboratory animals and poultry. An anti-inflammatory effective daily dosage of the active compounds as administered orally to humans comprises about 1 to 100, generally 2 to 50 and preferably 2 to 25 mg./kg., of body weight together with 1–5000 mg. of pharmaceutically acceptable carrier. The dose can be administered singly or as divided dosages throughout the day.

Oral administration is preferred, the compounds of this invention being particularly valuable in the treatment of humans afflicted with inflammation and pain, pyrexia, allergic diseases such as asthma and nettle rash, dermatological diseases, mastocytoma, hyperacidity, rheumatism, arthritis and hyperuricacidemia such as caused by gout and urate stones. In this regard, they can be employed in substantially the same manner as the known compound: e.g., phenylbutazone, mephenamic acid, bucolome.

It will be appreciated that the actual preferred amounts of active compounds used will vary according to the specific compound being utilized, the particular compositions formulated, the mode of application, and the particular situs and organism being treated. Many factors that modify the actions of drugs will be taken into account by those skilled in the art, e.g. age, body weight, sex, diet, time of administration, route of administration, rate of excretion, drug combinations, reaction sensitivities and severity of the particular disease. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples, the temperatures are set forth uncorrected in degree Celsius; unless otherwise indicated, parts and percentages are by weight.

DESCRIPTION OF THE PREFERRED EMBODIMENTS

EXAMPLE 1

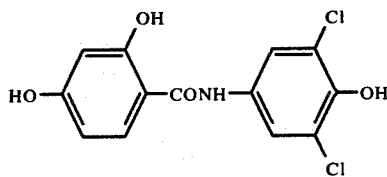

Preparation of 3,5-dichloro-2',4', 4-trihydroxybenzanilide

1. Preparation of Diacetyl-β-resorcylic Acid:

β-Resorcylic acid (15.4 g.) and triethylamine (42 ml.) were dissolved in dried acetone (150 ml.). After cooling at 0°–5° C., acetyl chloride (21.3 ml.) in small parts was added with stirring, and the precipitate of triethylamine hydrochloride which formed was filtered off. Then after removal of acetone by evaporation, the filtrate was acidified with a solution of 2 N-hydrochloric acid, yielding diacetyl-β-resorcylic acid as a precipitate. By recrystallization from aqueous acetone, prism-like crystals were obtained (21.4 g.). Yield: 90%. The melting point is 136°–139° C.

2. Preparation of 3,5-dichloro-2', ,4',4-trihydroxybenzanilide:

Diacetyl-β-resorcylic acid (13.4 g.) was admixed with thionyl chloride (100 ml.) with stirring to make a uniform solution. After reaction was completed, the excess thionyl chloride was removed by evaporation under reduced pressure. The residue, diacetyl-β-resorcyloyl chloride, was dissolved in dried acetone (100 ml.).

4-Amino-2,6-dichlorophenyl (10 g.) and N,N-dimethylaniline (10 ml.) were dissolved in acetone (100 ml.) to which, with stirring and under cooling at 0°–4° C., the acetone solution of diacetyl-β-resorcyloyl chloride was added dropwise. After several hours, the reaction mixture was made acidic with hydrochloric acid, and was subjected to evaporation under reduced pressure until the volume was halved. The resultant solution was added to 1 liter of 4 N hydrochloric acid and allowed to stand in the cold. Precipitates were obtained and dissolved in acetone. The acetone solution was made alkaline with 2 N sodium hydroxide and stirred for several hours at room temperature. Acidifying the solution to pH 1–2 with dilute hydrochloric acid gave precipitate which was recrystallized in aqueous acetone to give light yellow prism-like crystals of 3,5-dichloro-2',4',4-trihydroxybenzanilide (13.2 g.). Yield: 84.8%. The melting point is 235°–237° C.

EXAMPLE 2

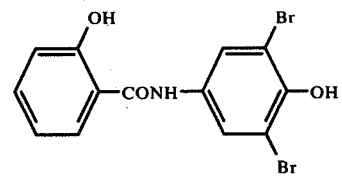

Preparation of 3,5-dibromo-2',4-dihydroxybenzanilide 2,6-Dibromo-4-aminophenol (0.6 g.) was dissolved in acetone (30 ml.) to which was added pyridine (0.32 ml.). Then dropwise and with stirring the solution was added to an acetone solution (10 ml.) containing acetylsalicyloyl chloride which was prepared from acetylsalicylic acid (0.38 g.). Then the reactant solution was evaporated to dryness under reduced pressure to give a residue which was dissolved in ethyl acetate. After washing first with water and then with 1 N hydrochloric acid, the solution was evaporated under reduced pressure to remove ethyl acetate. The residues were redissolved in a mixture of methanol and 2 N sodium hydroxide (10 ml. each). Stirring this solution for several hours and acidifying with 2 N hydrochloric acid precipitated the product which was recrystallized from aqueous methanol to give light brown crystals of 3,5-dibromo-2', 4-dihydroxybenzanilide (0.88 g.). Yield: 78%. The compound melts at 182°–187° C.

EXAMPLE 3

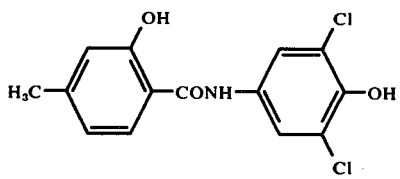

Preparation of 3,5-dichloro-2', 4-dihydroxy-4'-methyl-benzanilide

1. Preparation of 4-methyl-2-acetoxy-benzoic acid chloride:

4-Methyl-2-acetoxy-benzoic acid (18 g.) was dissolved in thionyl chloride (200 ml.), and the solution was left to stand overnight at room temperature. Removal of excess thionyl chloride by suction gave a paste of crude 4-methyl-2-acetoxy-benzoyl chloride which was dissolved in acetone (200 ml.).

Preparation of 3,5-dichloro-2', 4-dihydroxy-4'-methylbenzanilide

4-Amino-2,6-dichlorophenol (16 g.) was put into solution in N,N-dimethylaniline (15 ml) and acetone (200 ml.), to which the acetone solution of 4-methyl-2-acetoxybenzoyl chloride was added dropwise. After reaction for several hours, by condensing and then acidifying the solution with 4 N hydrochloric acid a precipitate was obtained, which was redissolved in 2 N sodium hydroxide solution. The solution was made acidic with dilute hydrochloric acid, thereby precipitating the product which was recrystallized from aqueous acetone to give white crystals (20.3 g.) of 3,5-dichloro-2',4-dihydroxy-4'-methylbenzanilide. Yield: 72.5%. The melting point was 246°–247° C.

EXAMPLE 4

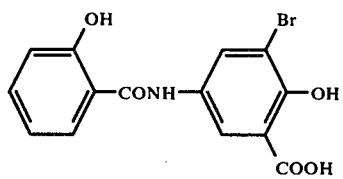

Preparation of 5-bromo-3-carboxy-2',4-hydroxy-benzanilide

3-Bromo-5-aminosalicylic acid (0.73 g.) was dissolved in acetone (30 ml.) and pyridine (0.4 ml.) to which an acetone (14 ml.) solution containing acetylsalicyloyl chloride (prepared from 0.53 g. of acetylsalicylic acid) was added dropwise with stirring. After reaction the solution was evaporated to dryness under reduced pressure and the residue was dissolved in ethyl acetate. After washing the solution with water and 1 N hydrochloric acid successively, the ethyl acetate was evaporated off under reduced pressure, yielding a residue which was redissolved in a mixture of methanol and 2 N sodium hydroxide (14 ml. each). After stirring the solution for several hours and then acidifying with 2 N hydrochloric acid solution, a precipitate was formed, collected and crystallized from aqueous methanol to give light brown crystals (0.90 g.) of 5-bromo-3-carboxy-2',4-dihydroxybenzanilide. Yield: 81.1%. Decomposition point: 275° C.

EXAMPLE 5

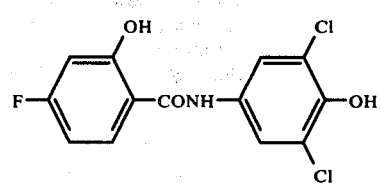

Preparation of 3,5-dichloro-2',4-dihydroxy-4'-fluorobenzanilide

4-Fluoroacetylsalicylic acid (10 g.) and thionyl chloride (70 ml.) were mixed and reacted with stirring until the solution became uniform and smooth. Then excess thionyl chloride was evaporated off under reduced pressure and the residual product was dissolved in acetone (200 ml.) to make an acetone solution of 4-fluoroacetylsalicyloyl chloride.

2,6-Dichloro-4-aminophenol (9.23 g.) and N,N-dimethylaniline (9 ml.) were dissolved in 250 ml. acetone, to which under cooling at −1° to 1° C. the acetone solution of 4-fluoro acetylsalicylic acid was added dropwise over 30–60 minutes. The reaction was continued with gentle stirring for several hours, after which about 150 ml. of acetone was removed by evaporation under reduced pressure and the residual condensate was admixed with 2 N sodium hydroxide solution and gently stirred for 24 hours. Acidification of the solution of pH 1–2 with hydrochloric acid gave a precipitate which was recrystallized from aqueous acetone to give white prism-like crystals (10.4 g.) of 3,5-dichloro-2',4-dihydroxy-4'-fluorobenzanilide. Yield: 64%. Melting point: 223°–224° C.

EXAMPLE 6

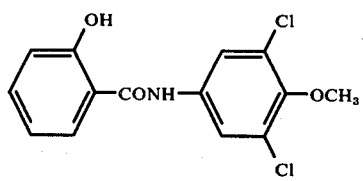

Preparation of 3,5-dichloro-2'-hydroxy-4-methoxybenzanilide

Acetylsalicyclic acid (1.8 g.) was converted to its acid chloride by conventional method using thionyl chloride and dissolved in acetone (30 ml.). 4-Amino-2,6-dichloroanisole (2.13 g.) with N,N-dimethylaniline (1.27 ml.) was dissolved in acetone (25 ml.) to which, with stirring in the cold at 0°–10° C., the above acetone solution of acetylsalicyloyl chloride was added dropwise over 20–30 minutes. Reaction continued for 1–2 hours, then the solution was evaporated to dryness under reduced pressure, the residue being put in sodium hydroxide solution and gently agitated for 1–2 hours for cleavage of the acetyl group. After reaction was complete the solution was made acidic by the addition of 2 N hydrochloric acid and the precipitate which formed was collected by filtration and recrystallized from aqueous acetone to give needle-like crystals (2.0 g.) of 3,5-dichloro-2'-hydroxy-4-methoxybenzanilide. Yield 64%. The melting point of the product is 226°–228° C.

EXAMPLE 7

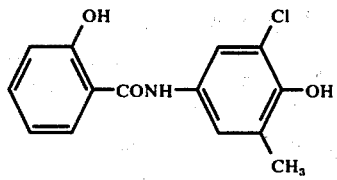

Preparation of 5-chloro-2',4-dihydroxy-3-methylbenzanilide

Acetylsalicyclic acid (1.39 g.) was converted to its acid chloride by conventional method using thionyl chloride and put in solution in acetone (25 ml.). 2-Methyl-4-amino-6-chlorophenol (1.35 g.) and N,N-dimethylaniline (about 1 ml.) were dissolved in acetone to which, with stirring in the cold at 1° to 2° C., the above-prepared acetone solution of acetylsalicyloyl chloride was added dropwise over 20–30 minutes, and reaction was continued for 1–2 hours. Then under reduced pressure the acetone was evaporated off, and the residue was put in solution in 2 N sodium hydroxide by stirring several hours at room temperature. Addition of 2 N hydrochloric acid to make the pH of the solution lower than 1 resulted in the formation of a precipitate which was recrystallized from aqueous acetone to give white crystals (1.08 g.) of 5-chloro-2',4-dihydroxy-3-methylbenzanilide. Yield: 45.4%. Melting point: 192°–194° C.

EXAMPLE 8

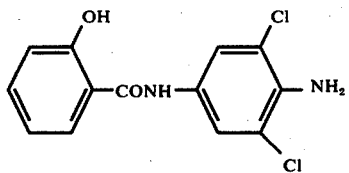

Preparation of 4-amino-3,5-dichloro-2'-hydroxybenzaniline

Acetylsalicylic acid (4.3 g.) was converted to its acid chloride in the conventional manner using thionyl chloride and dissolved in an acetone (35 ml.).

4-Amino-2,6-dichloroaniline (3.9 g.) was dissolved in acetone (40 ml.) to which was added N,N-dimethylaniline (2.8 ml.). With stirring and cooling at 0°–5° C. the above-prepared acetone solution of acetylsalicyloyl chloride was added dropwise and the reaction continued for several hours. Then by condensing the reactant solution there was obtained an oily material, which was dissolved in 2 N sodium hydroxide solution. That solution was gently stirred for several hours at room temperature for cleavage of the acetyl group. By acidifying the resultant solution with 2 N hydrochloric acid a precipitate was obtained. Since the desired compound existed as the hydrochloride salt in the precipitate, it was dissolved in methanol and neutralized with 2 N sodium hydroxide. After condensation, the solution was extracted with ethyl acetate. The solvent layer was washed with water, dried, and evaporated under reduced pressure, yielding a brown precipitate which was washed with methanol to give light brown crystals (3.9 g.) of 4-amino-3,5-dichloro-2'-hydroxybenzanilide. Yield: 59.6%. The product melts at 224°–227° C.

EXAMPLE 9

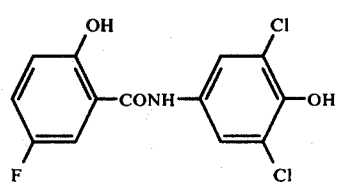

Preparation of 3,5-dichloro-2',4-dihydroxy-5'-fluorobenzanilide

5-Fluorosalicylic acid (5.15 g.) and 3,5-dichloro-4-hydroxyaniline (5.88 g.) were well mixed to which was added benzene (10 ml.) and N,N-dimethylaniline (4.35 ml.). Then with stirring thionyl chloride (3.3 ml.) was added and refluxed 30 minutes. The resulting solution was evaporated and the residue was dissolved in ethyl acetate and subjected to decolorization with activated charcoal followed by washing with 2 N hydrochloric acid and 2.5% sodium bicarbonate solution. The ethyl acetate was then extracted several times with 2 N sodium carbonate solution and the aqueous extracts were combined and brought to pH 1–2 with hydrochloric acid to give a precipitate which was recrystallized from aqueous acetone to give white needle-like crystals (5.7 g.) of 3,5-dichloro-2',4-dihydroxy-5'-fluorobenzanilide. Yield: 55%. Melting point: 227°–229° C.

EXAMPLE 10

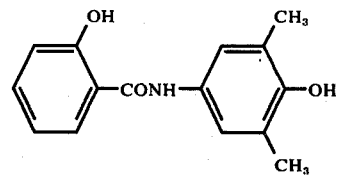

Preparation of 2',4-dihydroxy-3,5-dimethylbenzanilide

Acetylsalicyclic acid (50 mg.) and 4-amino-2,6-dimethylphenol (38 mg.) were dissolved in ethylene glycol (5 ml.) to which under cooling at 0° C. was added dicyclohexyl carbodiimide (65 mg.). After reaction for several hours the formed dicyclohexylurea was filtered off and the filtrate evaporated to dryness to give a powder which was dissolved in acetone (2 ml.); after adding 2 N sodium hydroxide (4 ml.), the solution was allowed to stand for several hours at room temperature. The addition of 2 N hydrochloric acid (20 ml.) gave a precipitate which was collected by filtration, washed with water and dried at 50° C. under reduced pressure to give solid 2',4-dihydroxy-3,5-dimethylbenzanilide as a powder which was then purified by column chromatography using Sephadex LH-20 resin and elution with methanol. The eluate was evaporated to dryness to give a solid which was recrystallized from aqueous acetone to give white crystals (57.8 mg.) of 2',4-dihydroxy-3,5-dimethylbenzanilide. Yield: 80.9%. Melting point: 142°–145° C.

EXAMPLE 11

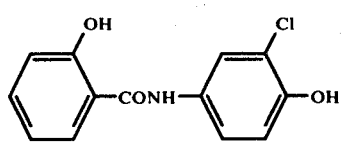

Preparation of 3-chloro-2',4-dihydroxybenzanilide

Salicyclic acid (1.38 g.) and 2-chloro-4-aminophenol (1.44 g.) were dissolved in acetonitrile (130 ml.), to which with stirring was added as a dehydrating agent dicyclohexyl carbodiimide (1.88 g.) and stirring was contained for about an hour. The precipitated dicyclohexylurea was filtered off, rinsed with warm acetone (90 ml.), and the filtrate and the rinse were combined and evaporated to dryness under reduced pressure. A light brown powder (2.57 g.) of 3-chloro-2',4-dihydroxybenzanilide was obtained which was purified through column chromatography using silica-gel (Mallinkrodt Co., U.S.A.) and an ethyl acetate-methanol mixture as the elution solution system to give needle-like crystals (0.18 g.) of 3-chloro-2',4-dihydroxybenzanilide. Yield: 7%. The melting point: 172.5°–173.5° C.

EXAMPLE 12

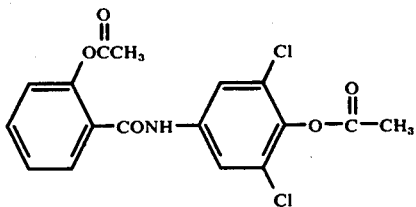

Preparation of 2',4-diacetoxy-3,5-dichlorobenzanilide

Acetylsalicycloyl chloride prepared by reaction of acetylsalicyclic acid with thionyl chloride was condensed with 4-amino-2,6-dichlorophenol, and then deacetylated to give 3,5-dichloro-2',4-dihydroxybenzanilide. That compound (4 g.) was dissolved in cold anhydrous acetic acid (50 ml.) and with stirring there was added with 3 drops of concentrated sulfuric acid. After reaction for 1–2 hours at 5°–6° C., the solution was poured into ice-cold water (500 ml.) and the white precipitate thus formed was collected by filtration, rinsed with water, dried and recrystallized from methanol to give white needle-like crystals (3.65 g.) of 2',4-diacetoxy-3,5-dichlorobenzanilide. Yield: 71.1%. Melting point: 154°–156° C.

EXAMPLE 13

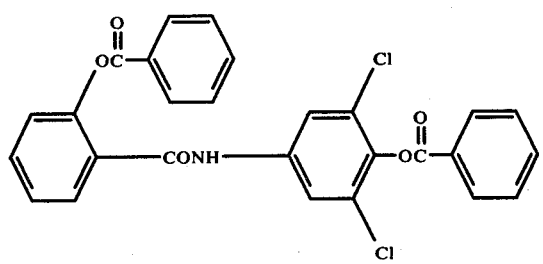

Preparation of 2',4-dibenzoyloxy-3,5-dichlorobenzanilide.

3,5-Dichloro-2',4-dihydroxybenzanilide (1 g.) was dissolved in dry pyridine (15 ml.) in the cold at 0°–5° C. and to it was added dropwise benzoyl chloride (1.2 ml.). With gentle stirring reaction was continued for several hours. The solution was then poured into ice-cold water and acidified with 1 N hydrochloric acid to pH 2, yielding oily material which was extracted by ethyl acetate. The ethyl acetate solution was washed with 1 N hydrochloric acid and 5% sodium bicarbonate solution in that order and dried with anhydrous sodium sulfate, followed by removal of the solvent by evaporation. The residue was subjected to recrystallization from ether and petroleum ether mixture to give white crystals (1.5 g.) of 2',4-dibenzoyloxy-3,5-dichlorobenzanilide. Yield: 88.2%. Melting point: 157°–160° C.

EXAMPLE 14

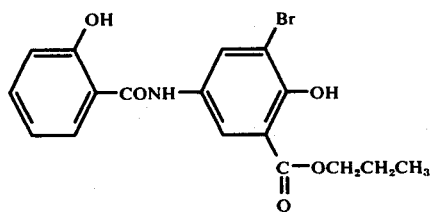

Preparation of 5-bromo-2',4-dihydroxy-3-n-propyloxycarbonylbenzanilide

5-Bromo-3-carboxy-2',4-dihydroxybenzanilide (1.0 g.) described in Example 4 was dissolved in n-propanol (50 ml.), and after adding conc. sulfuric acid (1 ml.) the solution was refluxed for 8 hours. After neutralizing with sodium hydroxide solution, the reaction solution was evaporated to dryness and the residue was washed with 5% sodium bicarbonate solution and recrystallized from aqueous acetone to give 5-bromo-2',4-dihydroxy-3-n-propyloxycarbonylbenzanilide (0.61 g.). Yield: 54.5% Melting point 198°–200° C.

EXAMPLE 15

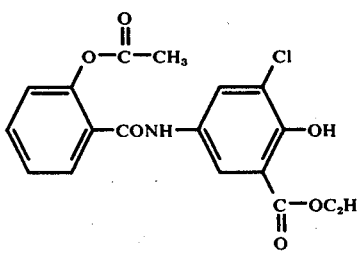

Preparation of 2'-acetoxy-5-chloro-3-ethoxycarbonyl-4-hydroxybenzanilide

3-Chloro-5-aminosalicylic acid ether ester (2.1 g.) was dissolved in benzene (60 ml.) and N,N-dimethyl aniline (1.3 ml.), to which with stirring at 40°–50° C. a benzene solution (30 ml.) containing acetylsalicycloyl chloride (2.0 g.) was added dropwise. Several hours later, the reaction mixture was washed with 1 N hydrochloric acid, then with 5% sodium bicarbonate solution, and the solvent was evaporated to give a solid which was recrystallized from aqueous acetone to give 2'-acetoxy-5-chloro-3-ethoxycarbonyl-4-hydroxybenzanilide. Yield: 74.0%. Melting point: 163°–166° C.

EXAMPLE 16

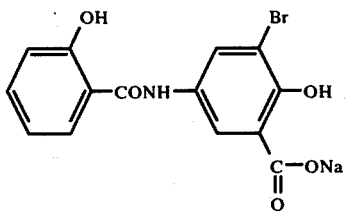

Preparation of 5-bromo-3-carboxy-2',4-dihydroxybenzanilide sodium salt

5-Bromo-3-carboxy-2',4-dihydroxybenzanilide (18 g.) described in Example 4 was dissolved in methanol (370 ml.) to which sodium hydroxide (2.76 g.) in aqueous solution (96 ml.) was added dropwise with stirring. The pH of the solution was adjusted to 7.6 – 7.8 and the methanol was evaporated. By cooling the condensed solution, precipitated crystals were obtained which were recovered by filtration, washed with acetone and dried under reduced pressure. Light yellow crystals of 5-bromo-3-carboxy-2',4-dihydroxybenzanilide sodium salt were obtained (14.2 g.). Yield: 74.5%. The decomposition point of the product is ca. 300° C.

EXAMPLE 17

Two kinds of tablets (A and B) suitable for oral administration and containing the following ingredients were prepared by conventional tabletting techniques.

| Ingredient: | Weight (mg.) |
|---|---|
| A) 3,5-Dichloro-2',4-dihydroxybenz-anilide | 250 |
| Sodium carboxymethylcellulose | 10 |
| Lactose | 213 |
| Corn starch | 25 |
| Magnesium stearate | 2 |
| B) 3,5-Dichloro-2',4-dipropionyloxybenz-anilide | 250 |
| Tragacanth | 10 |
| Lactose | 207 |
| Corn starch | 25 |
| Talcum | 5 |
| Magnesium stearate | 3 |

EXAMPLE 18

Two kinds of dry filled capsules (A and B) suitable for oral administration containing the following ingredients were prepared in conventional manner.

| Ingredient | Weight (mg.) |
|---|---|
| A) 3,5-Dichloro-2',4-dihydroxybenz-anilide | 250 |
| Inert solid diluent (e.g., Starch, Lactose) | 248 |
| Magnesium stearate | 2 |
| B) 3,5-Dichloro-2',4-dipropionyloxybenz-anilide | 250 |
| Inert solid diluent (e.g., Starch, Lactose) | 247.5 |
| Magnesium stearate | 2.5 |

The capsules so prepared are administered to a patient at a dose of 2 to 4 capsules a day.

The preceding examples can be repeated with similar success by substituting the generically or specifically described reactants and/or operating conditions of this invention for those used in the preceding examples.

We claim:

1. A method for chemotherapeutically treating a living animal having a biochemical disorder characterized by an abnormally high body level of histamine which comprises administering a compound having the formula

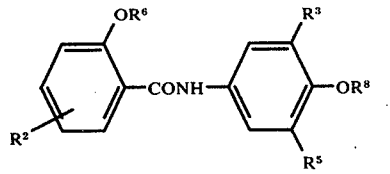

wherein $R^6$ and $R^8$ are alike and are benzoyl or alkanoyl; $R^2$ is substituted either at the 4'- position or at the 5'-position and is hydrogen, fluoro, bromo, chloro, hydroxy or lower alkyl; $R^3$ is chloro, bromo or lower alkyl; and $R^5$ is hydrogen, fluoro, bromo, chloro or lower alkyl to said animal in a dosage sufficient to lower said histamine level.

2. A method of claim 1 for chemotherapeutically treating a living animal having a biochemical disorder characterized by an abnormally high body level of histamine which comprises administering a compound having the formula

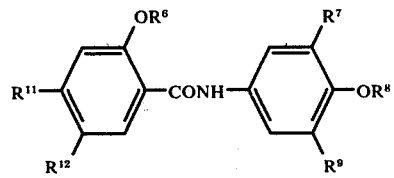

wherein $R^6$ and $R^7$ are alike and are benzoyl or alkanoyl; $R^7$ is chloro, bromo, methyl or ethyl; $R^9$ is hydrogen, chloro, bromo, lower alkyl or lower alkoxy; and one of $R^{11}$ and $R^{12}$ is hydrogen and the other is fluoro, bromo, chloro, hydroxy, methyl or ethyl to said animal in a dosage sufficient to lower said histamine level.

3. A method of claim 1 for chemotherapeutically treating a living animal having a biochemical disorder characterized by an abnormally high body level of histamine which comprises administering a compound having the formula

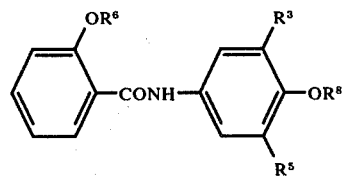

wherein $R^3$ is chloro, bromo or lower alkyl; $R^6$ and $R^8$ are alike and are benzoyl or alkanoyl; and $R^5$ is hydrogen, fluoro, bromo, chloro or lower alkyl to said animal in a dosage sufficient to lower said histamine level.

4. A method of claim 1 for chemotherapeutically treating a living animal having a biochemical disorder characterized by an abnormally high body level of histamine which comprises administering a compound having the formula

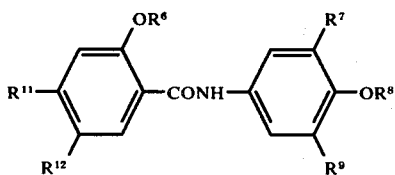

wherein $R^6$ and $R^8$ are alike and are alkanoyl; $R^7$ is chloro, bromo, methyl or ethyl, $R^9$ is hydrogen, chloro, bromo, lower alkyl or lower alkoxy; and one of $R^{11}$ and $R^{12}$ is hydrogen and the other is fluoro, bromo, chloro, hydroxy, methyl or ethyl to said animal in a dosage sufficient to lower said histamine level.

5. A method of claim 1 for chemotherapeutically treating a living animal having a biochemical disorder characterized by an abnormally high body level of histamine which comprises administering a compound having the formula

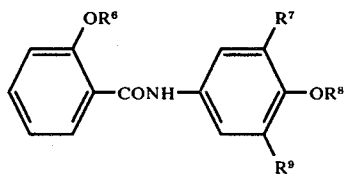

wherein $R^6$ and $R^8$ are alike and are benzoyl or alkanoyl; $R^7$ is chloro, bromo, methyl or ethyl and $R^9$ is hydrogen; chloro, bromo, lower alkyl or lower alkoxy to said animal in a dosage sufficient to lower said histamine level.

6. A method of claim 1 for chemotherapeutically treating a living animal having a biochemical disorder characterized by an abnormally high body level of histamine which comprises administering a compound having the formula

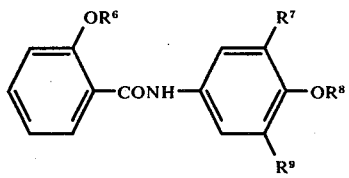

wherein $R^6$ to $R^8$ are alike and are benzoyl or alkanoyl; $R^7$ is chloro or bromo and $R^9$ is hydrogen, chloro, bromo, lower alkyl or lower alkoxy to said animal in a dosage sufficient to lower said histamine level.

7. A method of claim 1 for chemotherapeutically treating a living animal having a biochemical disorder characterized by an abnormally high body level of histamine which comprises administering the compound having the formula

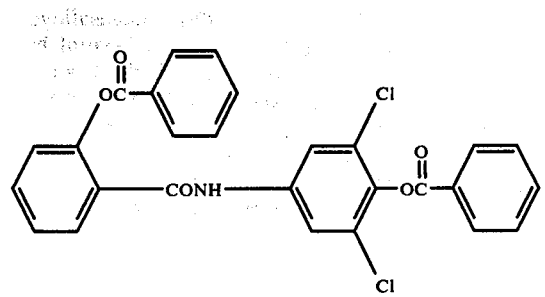

to said animal in a dosage sufficient to lower said histamine level.

8. A method of claim 1 for chemotherapeutically treating a living animal having a biochemical disorder characterized by an abnormally high body level of histamine which comprises administering the compound having the formula

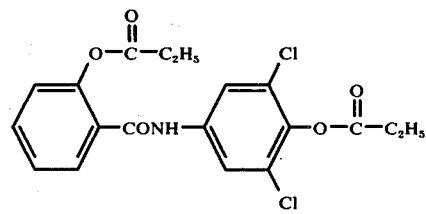

to said animal in a dosage sufficient to lower said histamine level.

9. A method of claim 1 for chemotherapeutically treating a living animal having a biochemical disorder characterized by an abnormally high body level of histamine which comprises administering the compound having the formula

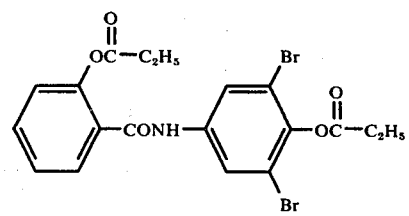

to said animal in a dosage sufficient to lower said histamine level.

10. A method for chemotherapeutically treating a living animal having a biochemical disorder characterized by an abnormally high body level of uric acid which comprises administering a compound having the formula

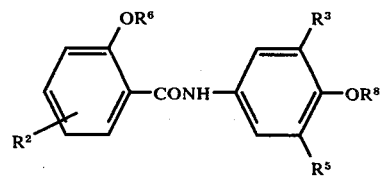

wherein $R^6$ and $R^8$ are alike and are benzoyl or alkanoyl; $R^2$ is substituted either at the 4- position or at the 5'-position and is hydrogen, fluoro, bromo, chloro, hydroxy or lower alkyl; $R^3$ is chloro, bromo or lower alkyl; and $R^5$ is hydrogen, fluoro, bromo, chloro or lower alkyl to said animal in a dosage sufficient to lower said uric acid level.

11. A method of claim 10 for chemotherapeutically treating a living animal having a biochemical disorder characterized by an abnormally high body level uric acid which comprises administering a compound having the formula

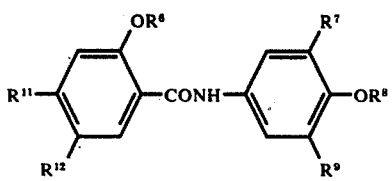

wherein $R^6$ and $R^8$ are alike and are benzoyl or alkanoyl; $R^7$ is chloro, bromo, methyl or ethyl; $R^9$ is hydrogen, chloro, bromo, lower alkyl or lower alkoxy; and one of $R^{11}$ and $R^{12}$ is hydrogen and the other is fluoro, bromo, chloro, hydroxy, methyl or ethyl to said animal in a dosage sufficient to lower said uric acid level.

12. A method of claim 10 for chemotherapeutically treating a living animal having a biochemical disorder characterized by an abnormally high body level of uric acid which comprises administering a compound having the formula

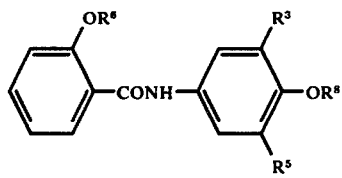

wherein $R^3$ is chloro, bromo or lower alkyl; $R^6$ and $R^8$ are alike and are benzoyl or alkanoyl; and $R^5$ is hydrogen, fluoro, bromo, chloro or lower alkyl to said animal in a dosage sufficient to lower said uric acid level.

13. A method of claim 10 for chemotherapeutically treating a living animal having a biochemical disorder characterized by an abnormally high body level of uric acid which comprises administering a compound having the formula

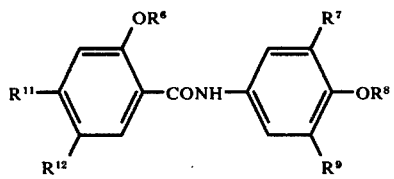

wherein $R^6$ and $R^8$ are alike and are alkanoyl; $R^7$ is chloro, bromo, methyl or ethyl, $R^9$ is hydrogen, chloro, bromo, lower alkyl or lower alkoxy; and one of $R^{11}$ and $R^{12}$ is hydrogen and the other is fluoro, bromo, chloro, hydroxy, methyl or ethyl to said animal in a dosage sufficient to lower said uric acid level.

14. A method of claim 10 for chemotherapeutically treating a living animal having a biochemical disorder characterized by an abnormally high body level of uric acid which comprises administering a compound having the formula

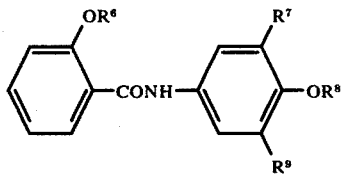

wherein $R^6$ and $R^8$ are alike and are benzoyl or alkanoyl; $R^7$ is chloro, bromo, methyl or ethyl and $R^9$ is hydrogen, chloro, bromo, lower alkyl or lower alkoxy to said animal in a dosage sufficient to lower said uric acid level.

15. A method of claim 10 for chemotherapeutically treating a living animal having a biochemical disorder characterized by an abnormally high body level of uric acid which comprises administering a compound having the formula

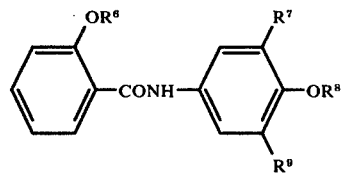

wherein $R^6$ and $R^8$ are alike and are benzoyl or alkanoyl; $R^7$ is chloro or bromo and $R^9$ is hydrogen, chloro, bromo, lower alkyl or lower alkoxy to said animal in a dosage sufficient to lower said uric acid level.

16. A method of claim 10 for chemotherapeutically treating a living animal having a biochemical disorder characterized by an abnormally high body level of uric acid which comprises administering the compound having the formula

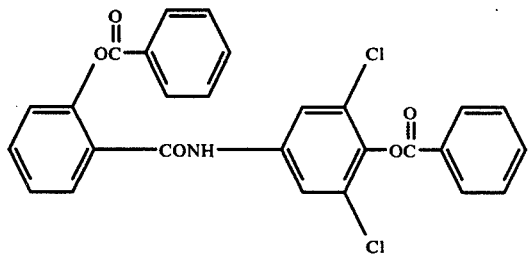

to said animal in a dosage sufficient to lower said uric acid level.

17. A method of claim 10 for chemotherapeutically treating a living animal having a biochemical disorder characterized by an abnormally high body level of uric acid which comprises administering the compound having the formula

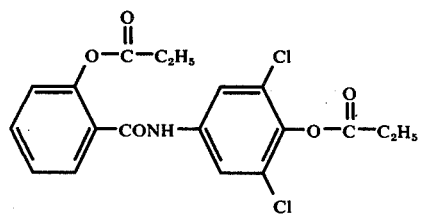

to said animal in a dosage sufficient to lower said uric acid level.

18. A method of claim 10 for chemotherapeutically treating a living animal having a biochemical disorder characterized by an abnormally high body level of uric acid which comprises administering the compound having the formula

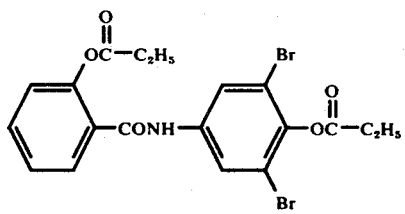
to said animal in a dosage sufficient to lower said uric acid level.
* * * * *